US009826932B2

(12) United States Patent
DeBusschere

(10) Patent No.: US 9,826,932 B2
(45) Date of Patent: Nov. 28, 2017

(54) AUTOMATED ABDOMINOJUGULAR REFLUX TESTING

(71) Applicant: Google Inc., Mountain View, CA (US)

(72) Inventor: Brian Derek DeBusschere, Los Gatos, CA (US)

(73) Assignee: Google LLC, Mountain View, CA (US)

( * ) Notice: Subject to any disclaimer, the term of this patent is extended or adjusted under 35 U.S.C. 154(b) by 16 days.

(21) Appl. No.: 15/133,076

(22) Filed: Apr. 19, 2016

(65) Prior Publication Data

US 2017/0296119 A1    Oct. 19, 2017

(51) Int. Cl.
*A61B 5/00*    (2006.01)
*A61B 5/024*    (2006.01)
*A61H 9/00*    (2006.01)

(52) U.S. Cl.
CPC .......... *A61B 5/4884* (2013.01); *A61B 5/0013* (2013.01); *A61B 5/0077* (2013.01); *A61B 5/024* (2013.01); *A61B 5/486* (2013.01); *A61B 5/684* (2013.01); *A61B 5/6898* (2013.01); *A61B 5/742* (2013.01); *A61H 9/0092* (2013.01); *A61B 2576/02* (2013.01); *A61H 2205/083* (2013.01)

(58) Field of Classification Search
None
See application file for complete search history.

(56) References Cited

U.S. PATENT DOCUMENTS

2013/0191605 A1    7/2013    Solihin
2013/0274638 A1*    10/2013    Jennings ............. A61M 1/0066
                                                                601/10
2014/0236058 A1*    8/2014    Lee ..................... A61B 17/1355
                                                                601/84
2014/0281110 A1    9/2014    Duluk et al.
2015/0067258 A1    3/2015    Jung et al.
2016/0249826 A1*    9/2016    Derchak ................. A61B 5/024

FOREIGN PATENT DOCUMENTS

EP    0362880    4/1990
EP    0472868    3/1992
EP    1505506    2/2005
WO    2017139037    8/2017

* cited by examiner

*Primary Examiner* — Ankit D Tejani
(74) *Attorney, Agent, or Firm* — Colby Nipper

(57) ABSTRACT

This document describes automated abdominojugular reflux (AJR) testing. To automate AJR tests, a pressure cuff wrapped around a person's abdomen applies pressure while video of their neck is captured. By way of example, a medical professional wraps a pressure cuff around the person's abdomen and records video of the person's neck using a smartphone, which communicates with the pressure cuff to synchronize the application of pressure with video capture. The video is processed to detect and track the response of jugular venous pulse (JVP), which is compared to AJR test thresholds to determine test results. While determining JVP, and thereby results of AJR tests, from reconstructed videos may not result in data that is as accurate as invasive intra-heart tests, it requires little if any risk to patients and is easy for medical professionals to perform. Further, these techniques enable AJR tests to be performed automatically and without relying on estimates made by skilled medical professionals.

20 Claims, 7 Drawing Sheets

AUTOMATED ABDOMINOJUGULAR REFLUX TESTING

BACKGROUND

As part of monitoring patients' health, medical professionals evaluate patients' cardiovascular systems through cardiac physical exams. One of the tests that is useful to medical professionals in evaluating a patient's cardiovascular system is an abdominojugular reflux (AJR) test, which is used as a marker for indicating cardiac dysfunction.

In accordance with conventional AJR-testing techniques, a medical professional applies slow, steady pressure to an abdominal region of a patient while observing the patient's neck for a minimum period of 10 seconds. During that time, the medical professional observes the patient's neck to monitor changes in their jugular venous pressure by watching for changes in the person's jugular venous pulse (JVP). In healthy patients, the JVP rises less than 3 centimeters from an initial location and then falls down even while pressure is maintained. This is considered a "normal" response, and results in a negative AJR test—one indication of good cardiovascular health. If the observed JVP remains above 3 centimeters during the 10 seconds of sustained pressure and drops abruptly by more than 4 centimeters upon release of the pressure, however, the result of the AJR test is positive. A positive AJR test is a highly specific indicator of potential problems with the patient's heart, namely, it indicates that a right side of the patient's heart is unable to accommodate an increase in venous return.

Conventional techniques for performing AJR tests are inconsistent due to variations in the skill level and techniques across medical professionals, however. Such techniques are inconsistent because they rely on tracking changes in the difficult to observe JVP. The JVP is a faint and difficult to discern signal that requires a significant degree of training to reliably identify. As such, AJR tests are performed almost solely by skilled physicians, making their use outside a clinic or hospital environment cost prohibitive. The drawbacks of conventional AJR-testing techniques render them less than ideal in many cases.

SUMMARY

This document describes automated abdominojugular reflux testing. To automate an abdominojugular reflux (AJR) test, a pressure cuff wrapped around a person's abdomen applies a slow, steady pressure to a particular region and video of the person's neck is captured while the pressure is applied. By way of example, a medical professional wraps a pressure cuff around the person's abdomen and records a video of a right side of the person's neck using a smartphone, which communicates with the pressure cuff to synchronize application of the pressure with the video capture. The right side of the person's neck is preferably captured because it is where the person's right internal jugular vein is located and that vein fills vertically based on the jugular venous pressure, observable by watching the jugular venous pulse (JVP). The right side is preferable to the left side since it is closer to the right atrium. It is also preferable to capture the internal jugular vein over the external jugular vein since it has a more direct path to the atrium.

The video is then processed to detect the JVP. By way of example, video motion amplification techniques may be applied to generate a reconstructed video of the right side of the person's neck, e.g., by an application on the smartphone of the medical professional. From the reconstructed video the JVP can be automatically detected and tracked to record changes in location over time in response to the applied pressure. The change in location of the JVP over time in response to the applied pressure is referred to as a "dynamic response" of the JVP. Using the reconstructed video, the dynamic response can be quantified and compared to one or more AJR test thresholds to determine a result of the AJR test. A positive AJR test result is a highly specific indicator of a person's impaired cardiac functional performance.

AJR test thresholds can include a system self-test, a JVP detectability threshold, a minimum initial rise threshold, a minimum sustained rise threshold, and a minimum descent threshold. If the system self-test fails to pass a threshold or the automated JVP detection and tracking algorithms are unable to detect the JVP location with sufficient confidence to pass the JVP detectability threshold, then the test result will be indeterminate. In accordance with the techniques described herein, a positive AJR test result is generated when the minimum initial rise threshold, the minimum sustained rise threshold, and the minimum descent thresholds are each satisfied. The failure to satisfy any one of those thresholds may result in a negative AJR test result. While determining JVP, and thus the results of an AJR test, from a reconstructed video may not result in data that is as accurate as an invasive intra-heart test, for example, it requires little if any risk to the person and is easy for a medical professional to perform. Further, the techniques described herein enable AJR tests to be performed automatically and without relying on estimates made by skilled medical professionals.

This summary is provided to introduce simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for automated abdominojugular reflux testing are described with reference to the following drawings. The same numbers are used throughout the drawings to reference like features and components.

DETAILED DESCRIPTION

Overview

Figure 1:
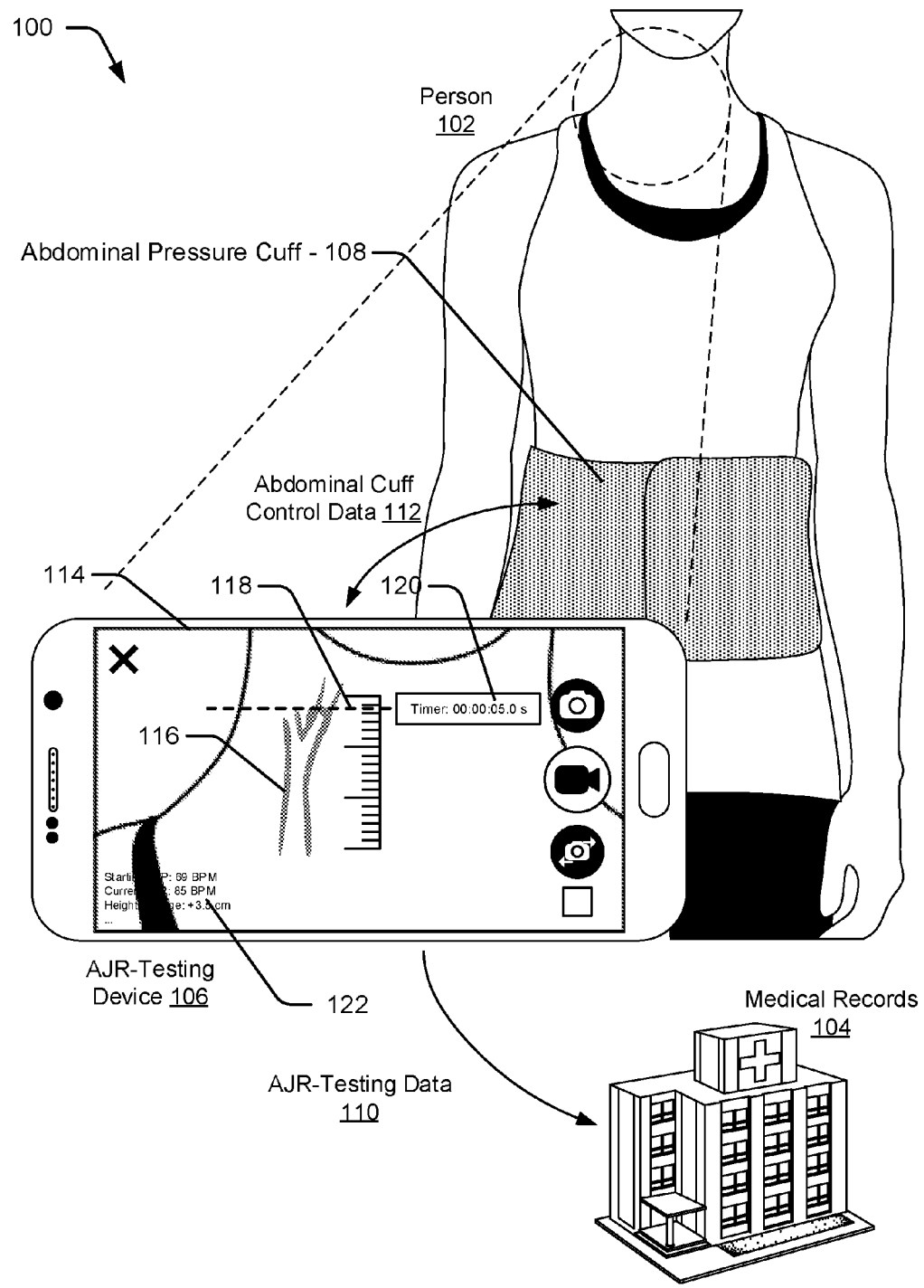
FIG. 1 illustrates an example environment in which the techniques can be implemented.

This document describes techniques using, and devices enabling, automated abdominojugular reflux (AJR) testing. Through use of these techniques and devices, AJR testing for a person can be automated and with greater reproducibility than the current clinical protocol, which relies on the application of slow, steady pressure to the person's abdomen by a medical professional and at the same time making difficult visual estimates at another region of the person's body. Moreover, the techniques described herein can reduce the role of the medical professional in performing AJR tests for a person to wrapping a suitably configured pressure cuff around the person's abdomen and positioning an AJR-measuring device in a position where video of the person can be captured. In some embodiments, the AJR-testing can be automated to an extent that enables a person to self-administer the test. Through wide application of these techniques, AJR tests can be performed consistently and without exposing patients to invasive procedures.

By way of example, a medical professional can wrap an abdominal pressure cuff around a person that is configured to apply slow, steady pressure to a particular region of their abdomen. The medical professional can hold an AJR-testing device, such as a smartphone configured with a video camera and an AJR-testing application, to communicate with the pressure cuff to initiate application of the pressure and capture video of a right side of a person's neck. The captured video can then be processed by the application to detect the person's jugular venous pulse (JVP) and measure a dynamic response of the JVP while application of the pressure is initiated, maintained, and released. Using the captured video, for instance, components of the application can take measurements of the person's JVP and jugular distension that are indicative of the dynamic response of the person's JVP and pertinent to performing an AJR test, such as a change in location of the JVP over time as the pressure is applied, sustained, and released.

The AJR-testing application can then compare the measurements indicative of the dynamic response of the person's JVP (e.g., measurements indicating the change in location of the JVP) to thresholds associated with AJR tests to determine a result of the AJR test—an indicator of the person's cardiac functional performance. By way of example, one such threshold may correspond to a minimum initial rise threshold for the JVP. If a comparison of the initial rise in the person's JVP (detected from the captured video) indicates that it does not exceed the threshold rise within a set interval after the pressure cuff applies pressure to their abdomen, then the result of the test is determined to be negative. Another threshold associated with AJR tests is a minimum sustained rise threshold where the rise in the JVP must be sustained above a minimum level during a set time interval of applied pressure to result in a positive test. If, for example, it is determined that the person's JVP does rise above the initial rise threshold during the test, but then falls below the minimum sustained rise threshold within a set time interval while pressure is still applied, then the result of the test is again determined to be negative. If the person's JVP remains above the sustained rise threshold for the set time interval, however, a positive test result may be determined. Another threshold is a minimum descent threshold—if the JVP falls by at least a minimum amount within a short time interval after pressure is released, a positive result is generated. While these thresholds are consistent with the current standard of care, the ability of the automated system to more efficiently and reproducibly quantify the response of the JVP to the applied pressure will allow for the development of new thresholds to improve sensitivity and specificity as well as more diagnostic resolution than mere binary—pass or fail—results. For example, a peak height, rise and fall times, and other metrics may be quantified and trended over time.

A result of the AJR test can then be presented to the medical professional in a user interface, for example, on a display of the smartphone of the medical professional. In some cases, the user interface may display the captured video of the person's neck and an overlay that presents information, including determined JVP, dynamic response of the JVP over the test, elapsed time for an elevated JVP, a height of blood rise, and the like, to the medical professional. The user interface may also display instructions regarding how to set up an automated AJR test. The instructions can describe how to wrap the pressure cuff around the person's abdomen to enable an AJR test to be performed. Further, the instructions can indicate that the pressure cuff is not suitably positioned or wrapped around the person and can thus also provide additional feedback for appropriately adjusting the pressure cuff Based on information from sensors in the pressure cuff, the user interface can present notifications that indicate the pressure cuff has been suitably positioned and that an AJR test can be initiated.

Thus, with the small effort of wrapping a pressure cuff around a person's abdomen and holding a device in a position to record pulsatile motion in the person's venous system, a consistent AJR test can be performed in a relatively short amount of time. When performed on a repeated basis and over a period of time (e.g., every few hours for a day, days, or weeks), this act can be used to determine a trend of the person's AJR tests. Consider that, over the course of treatment involving intravenous fluid resuscitation, the techniques, using videos captured with the AJR-testing device, can determine that the person's AJR tests have become consistently negative over a period of time. Using such techniques, medical professionals may avoid invasive testing procedures, thereby likely reducing the chances of injury from the trauma associated with those procedures.

This is but one simple example of ways in which automated abdominojugular reflux testing can be performed, other examples and details are provided below. This document now turns to an example environment, after which example automated abdominojugular reflux testing devices, user interfaces, and methods, as well as an example computing system are described.

Example Environment

FIG. 1 is an illustration of an example environment 100 in which automated abdominojugular reflux (AJR) testing can be employed. Environment 100 illustrates a person 102 that is the subject of the AJR testing, as well as medical records 104 that, in some cases, store results of the automated AJR test. This example employs AJR-testing device 106 that is capable of automating AJR tests by communicating with abdominal pressure cuff 108 to synchronize the application of slow, steady pressure to a particular region of the person 102's abdomen with optical measurement of the person's jugular venous pulse (JVP) and jugular distension. In the particular example of FIG. 1, the AJR-testing device 106 is configured as a smartphone, however, other configurations are contemplated. Other configurations of the AJR-testing device 106 for automating AJR tests are illustrated in later figures.

AJR-testing data 110 is communicable from the AJR-testing device 106 to other entities, such as a service provider that stores the medical records 104, some other computing device remote from the AJR-testing device (not shown), and so on. The AJR-testing data 110 can include data indicative of a JVP and jugular distension detected during an AJR test by the AJR-testing device 106. Alternately or additionally, the AJR-testing data 110 can include raw video captured by the AJR-testing device 106 to track the JVP, reconstructed video that results from processing the captured video according to one or more video motion amplification or other enhancement techniques, measurements of the JVP over time in relation to applied pressure (which can be indicative of a dynamic response of the JVP to the applied pressure), quantitative metrics such as the initial rise, sustained rise, initial descent, or heart rate, final test results, and so forth. Since each of these different types of data (which, in effect, represent different portions in the process of performing AJR tests using captured video) can be communicated to remote computing devices, the different portions of the AJR-testing process can be performed at various computing devices. By so doing, the computing burden of automating AJR tests is capable of being offloaded from the AJR-testing device 106.

Additionally, in the case of home health care or remote telemedicine, communication of the AJR-testing data 110 enables the measurements to be reviewed for accuracy remotely by a trained medical professional as well as for remote treatment decisions such as adjusting prescriptions or triggering a clinic visit. For example, a telemedicine service provider may be configured to remotely review the AJR-testing data 110 and based on the review make treatment changes or suggest potential treatment changes to a medical provider associated with the person 102. A telemedicine service provider may adjust diuretics, for instance, based on a remote review of the AJR-testing data 110.

Generally, the AJR-testing device 106 is capable of communicating abdominal cuff control data 112 data to and receiving it from the abdominal pressure cuff 108 to control application of pressure to the person 102's abdomen when performing AJR tests. By way of example, when conducting an AJR test, the AJR-testing device 106 communicates the abdominal cuff control data 112 to the abdominal pressure cuff 108 to initiate application of a slow, steady pressure to a particular region of the person 102's abdomen. When the AJR test is complete, the AJR-testing device 106 can communicate the abdominal cuff control data 112 to the abdominal pressure cuff 108 to cease application of the applied pressure.

The AJR-testing device 106 is also capable of capturing video of the person 102. By way of example, the AJR-testing device 106 captures video of the person using a camera that is included as part of the AJR-testing device 106 while the abdominal pressure cuff 108 applies the pressure. The AJR-testing device 106 synchronizes application of the pressure with the video capture. By "synchronize" it is meant that the AJR-testing device 106 begins capturing video before pressure is applied to the person 102's abdomen, continues capturing video through application of the pressure, and stops capturing video at some time after the abdominal pressure cuff 108 ceases applying the pressure. After processing the captured video, the AJR-testing device 106 is capable of detecting the person 102's JVP, and thus determining a result of the AJR test, as described herein below.

As noted above, conventional techniques for performing AJR tests involve a medical professional applying slow steady pressure to a particular region of the person 102's abdomen, and observing the person 102's neck to watch their JVP, an indication of the person 102's jugular venous pressure. Generally, a person's JVP can be observed through pulsatile motions in the person 102's neck that result from blood flowing into the person's internal jugular vein as their heart beats. In healthy patients, the JVP rises less than 3 centimeters and then falls down even while pressure on the abdomen is maintained. This is considered a "normal" response, and results in a negative AJR—one indication of good cardiovascular health.

If the observed JVP remains elevated above 3 centimeters from an initial location during the 10 seconds of sustained pressure and drops abruptly by more than 4 centimeters upon release of the pressure, however, the result of the AJR test is positive. A positive AJR test is a highly specific indicator of potential problems with the patient's heart, namely, it indicates that a right side of the patient's heart is unable to accommodate an increase in venous return. Consequently, these techniques rely, in large part, on the ability of a test administrator (e.g., a medical professional) to apply a slow, steady pressure to the person 102's abdomen and simultaneously estimate relative pulsatile motion characteristics, such as rates, height, elapsed time that certain rates persist, and so on.

Even assuming that a medical professional is capable of consistently applying a slow, steady pressure and, at the same time, accurately and consistently estimating the different characteristics of pulsatile motions, some pulsatile motions that correspond to JVP are so subtle that they are imperceptible to the human eye. Unlike conventional non-invasive AJR-testing techniques, the techniques described herein can amplify the human imperceptible motion to make it visible. Further, when the measuring is performed by components of the AJR-testing device 106, these techniques do not rely on an observer to estimate characteristics of JVP-related pulsatile motions that occur in the person 102's neck. Instead, the AJR-testing device 106 can determine JVP and characteristics of the pulsatile motions from a video of the person 102 in which pulsatile motion may be visually amplified. Consequently, the involvement of medical professionals in AJR testing may be reduced to simply wrapping the abdominal pressure cuff 108 around the person 102 and placing the AJR-testing device 106 in a position where video of the person 102's neck can be captured.

As shown with the example environment 100, the AJR-testing device 106 is capable of displaying a user interface 114 to present video of the person 102's neck, such as reconstructed video in which pulsatile motion occurring in the person 102's neck is visually amplified. The user interface 114 includes visually-amplified pulsatile motion 116, for example, which is not shown on the person 102. Thus, the example environment 100 represents a scenario in which the pulsatile motion may be imperceptible to the human eye but is amplified according to one or more video motion amplification techniques to be visible in the reconstructed video. Additionally, playback of the reconstructed video can be time stretched (e.g., so that it is played back in slow motion) to allow for easier identification of jugular distension and identification of a time intervals. The user interface 114 also includes several indications overlaying the reconstructed video, including a line 118 indicative of the rise of JVP relative to an initial detected location of the person 102's JVP that indicates vertical orientation and distance, a timer 120 capable of indicating an amount of time the rise in the person's JVP is above a threshold rise, and measurements 122 corresponding to different metrics automatically acquired from the video and associated with conducting AJR tests. Optionally, the patient's heart rate and respiration rate may also be shown in the user interface 114, automatically detected by monitoring temporal chroma changes or motion in the video. In the case of use by minimally trained personnel, the user interface 114 can present anatomical guidance overlays to help guide proper orientation of the camera. The user interface 114 can also present a result of a given AJR test, such as whether the AJR-test result is positive, negative, or indeterminate.

Figure 2:
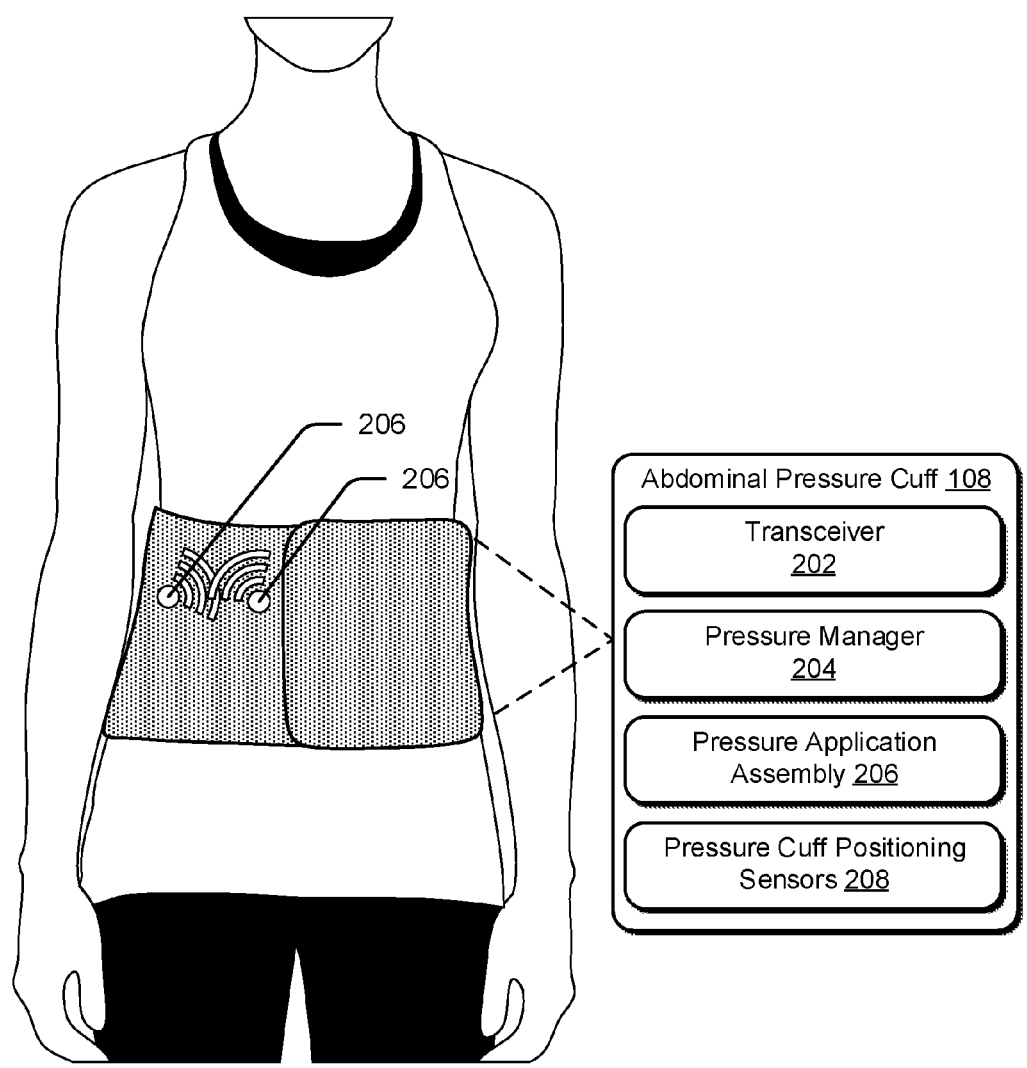
FIG. 2 illustrates an example of an abdominal pressure cuff usable to automate abdominojugular reflux (AJR) testing.

With regard to the example abdominal pressure cuff 108 of FIG. 1, consider a detailed illustration in FIG. 2. The abdominal pressure cuff 108 can be configured as a band that wraps around the person's waist. By way of example, the abdominal pressure cuff 108 may be configured as a belt-like band made of one or more fabrics that wraps around the person's waist and is secured in position, e.g., using a hook and look closure, buttons, a ring that allows the belt to double-back on itself to secure the belt through friction, tie downs, and so on. The abdominal pressure cuff 108 may also be configured as a continuous loop of stretchy material that the person 102 can step into and which can be slid up the person 102 until it is positioned around their abdomen. In other implementations, the abdominal pressure cuff 108 may be integrated with a garment worn by the person 102, such as a compression shirt, girdle, and so on. In any case, the abdominal pressure cuff 108 is configured so that it can be worn at least temporarily to apply pressure primarily to a particular portion of the person 102's abdomen.

The abdominal pressure cuff 108 includes or is able to communicate with a transceiver 202, pressure manager 204, pressure application assembly 206, and pressure cuff positioning sensors 208. The transceiver 202 is capable of sending and receiving data directly or through a communication network, such as sending the abdominal cuff control data 112 to and receiving it from the AJR-testing device 106 through a local area, wide area, personal area, cellular, or near-field network. Although FIG. 1 illustrates an implementation in which the abdominal pressure cuff 108 wirelessly communicates with the AJR-testing device 106, the transceiver 202 may also be capable of sending and receiving data over a wired connection with the AJR-testing device 106. Thus, the abdominal pressure cuff 108 and the AJR-testing device 106 may be configured to implement the techniques described herein over a wired and/or wireless connection.

The pressure manager 204 represents functionality of the abdominal pressure cuff 108 to manage application of pressure to the person 102's abdomen in conjunction with performing an AJR test. By way of example, the pressure manager 204 can cause the pressure application assembly 206 to apply a slow, steady pressure to a particular abdominal region of the person 102. The pressure manager 204 can also cause the pressure application assembly 206 to cease application of pressure to the person 102's abdomen.

When an AJR test is initiated (e.g., responsive to a user selection at the AJR-testing device 106 to initiate the AJR test), the AJR-testing device 106 may communicate the abdominal cuff control data 112 to the abdominal pressure cuff 108. In this case, the abdominal cuff control data 112 can indicate that the AJR test is to begin and to initiate application of pressure to person 102's abdomen. In response, the pressure manager 204 can employ the pressure application assembly 206 to apply pressure to the person 102's abdomen for the AJR test. After a time associated with performing AJR tests lapses, the pressure manager 204 can cause the pressure application assembly 206 to cease applying pressure to the person 102's abdomen. The pressure manager 204 may do so, for instance, after receiving additional abdominal cuff control data that indicates the test is complete or it is time for a next step in the test and to cease application of the pressure. Alternately or in addition, the pressure manager 204 may maintain a timer and cause the pressure application assembly 206 to cease applying pressure when the timer indicates the time associated with applying pressure during AJR tests has lapsed.

Although the pressure manager 204 may be configured to cause the pressure application assembly 206 to vary an amount of pressure applied to the person 102's abdomen, a length of time the pressure is applied, and even a location where the pressure application assembly applies the pressure, the pressure manager 204 can also employ the pressure application assembly 206 to consistently apply a specific amount of pressure for a specific amount of time and to a specific location of the person 102. In one or more implementations, for instance, the pressure manager 204 employs the pressure application assembly 206 to apply about 20-35 millimeters of mercury (mmHg) of pressure to the person 102's abdomen for a predetermined period of time ranging from 10-15 seconds. Alternatively, the AJR-testing device 106 may initiate a feedback loop with the abdominal pressure cuff 108, which enables the applied pressure to be ramped up in stages to minimize potential patient discomfort. If 20 mmHg of pressure is sufficient to create an initial rise in the person 102's JVP, for instance, the abdominal pressure cuff 108 may not be commanded to ramp up to 35 mmHg. The minimum applied pressure number that generates an initial rise in JVP may also be used as a diagnostic metric.

In general, the pressure application assembly 206 represents functionality of the abdominal pressure cuff 108 to apply a specified amount of pressure to a specified location. The pressure application assembly 206 may be formed of multiple pressure-applying components (e.g., pockets configured to inflate and deflate to specified mmHg), each of which is capable of applying a specified amount of pressure. The pressure manager 204 may select which of the pressure applying components are to be activated to control a location at which the pressure is applied, and such that a subset of the components is used to apply pressure to the location. Furthermore, the pressure manager 204 may be able to control an amount of pressure each of the activated pressure applying components applies. Alternately the pressure application assembly 206 may be formed of a single component (e.g., a single inflatable pocket), which the pressure application assembly 206 can control to apply the specified amount of pressure to the person 102's abdomen. The pressure application assembly 206 may be configured in a variety of different ways to apply pressure under the control of the pressure manager 204 without departing from the spirit or scope of the techniques described herein.

The pressure cuff positioning sensors 208 represent any of a variety of different sensors that are capable of detecting a position of the abdominal pressure cuff 108 relative to the person 102's abdomen. By way of example, the pressure cuff positioning sensors 208 can be configured to detect whether the abdominal pressure cuff 108 has been wrapped around the person 102 in a manner that positions the pressure application assembly 206 so that when it applies pressure, the pressure is applied to the region of the person 102's abdomen associated with AJR tests. The pressure cuff positioning sensors 208 are also capable of detecting other positioning characteristics that enable an AJR test to be performed without error, such as whether the abdominal pressure cuff 108 is wrapped tightly enough around the person 102, whether the abdominal pressure cuff 108 is secured, an orientation of the abdominal pressure cuff 108 relative to a target positioning (e.g., it is too low, too high, needs to be rotated to the right, rotated to the left), and so forth. In any case, the pressure cuff positioning sensors 208 can detect a variety of different information about the positioning of the abdominal pressure cuff 108 relative to the person. This information can be communicated to the AJR-testing device 106 as part of the abdominal cuff control data 112. Using this, the AJR-testing device 106 can alert a user when the abdominal pressure cuff 108 is not properly positioned for an AJR test and also when the user can select to initiate an AJR test, e.g., because the abdominal pressure cuff 108 is properly positioned for performing AJR tests.

Figure 3:
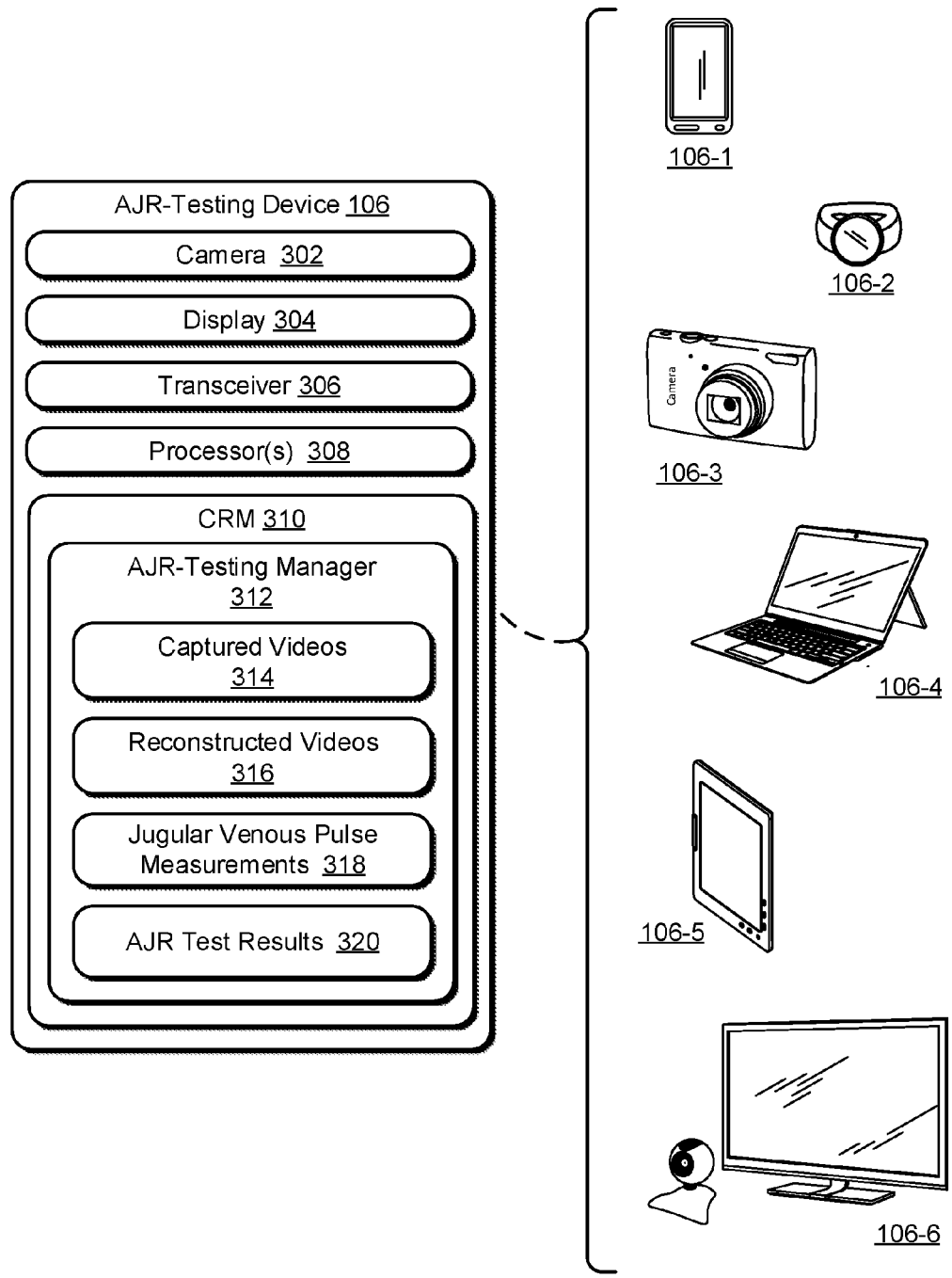
FIG. 3 illustrates an example AJR-testing device of FIG. 1.

With regard to the example AJR-testing device 106 of FIG. 1, consider a detailed illustration in FIG. 3. The AJR-testing device 106 can be one or a combination of various devices, here illustrated with six examples: a smartphone 106-1, a computing watch 106-2, a digital camera 106-3, a laptop 106-4, a tablet computer 106-5, and a desktop computer coupled to an external camera device 106-6 though other computing devices and systems, such as a netbook or a specialized imaging device with a particular configuration of AJR-testing sensors may also be used. As noted above, in some embodiments the techniques operate, at least in part, through a remote computing device. The remote computing device can be configured as a server, for example. In such cases, some computing can be forgone locally, e.g., through a communication device having limited computing operations or even directly from AJR-testing devices 106 to the server.

The AJR-testing device 106 includes or is able to communicate with a camera 302, a display 304 (five are shown in FIG. 3), a transceiver 306, one or more processors 308, and computer-readable storage media 310 (CRM 310). The transceiver 306 is capable of sending and receiving data directly or through a communication network, such as the AJR-testing data 110 or the abdominal cuff control data 112 from devices 106 through a local area, wide area, personal area, cellular, or near-field network.

The camera 302 represents functionality of the AJR-testing device 106 to capture video of a scene, such as one that includes the person 102. In addition to capturing video, the camera 302 may be capable of capturing still images, zooming in or out to capture video and still images, and the like. With reference to the example environment 100, the camera 302 may be included in the AJR-testing device 106 on a side opposite the display presenting the user interface 114. In this way, the user interface 114 can be used as a viewfinder for the camera 302. In some embodiments, the viewfinder can be disposed on the same side of the AJR-testing device 106 as the camera, facilitating self-assessment. The AJR-testing device 106 may also be configured with additional cameras, or the camera 302 configured with functionality in addition to capturing video and images. By way of example, the AJR-testing device 106 may be configured to include hyperspectral cameras, e.g., visual and infrared. Hyperspectral cameras can be used to improve the ability of the AJR-testing device 106 to locate veins and arteries of interest and monitor pulsatile motion. The AJR-testing device 106 may also be configured to include a dedicated depth-sensing camera and a high-frame rate camera. A dedicated depth sensing camera can be used to increase sensitivity to motion and a high-frame rate camera can be used to improve temporal recording of the jugular distensions.

The AJR-testing device 106 can be configured with still other components to aid in detecting pulsatile motion, visually amplifying the pulsatile motion, and measuring characteristics of the pulsatile motion. By way of example, the AJR-testing device 106 can be configured with lasers or light emitting devices that emit structured light to enable a greater degree of sensitivity in motion detection. The AJR-testing device 106 can also be configured to use tangential light sources to enhance the motion through changes in shadowing that improve a contrast of the motion relative to other portions of the person 102 (e.g., other portions of their skin). The AJR-testing device 106 may be configured with various combinations of optical components without departing from the spirit or scope of the techniques described herein.

The CRM 310 includes AJR-testing manager 312, which includes or has access to captured videos 314, which are output by the camera 302. The CRM 310 also includes reconstructed videos 316 which are generated by processing the captured videos 314 according to one or more video motion amplification or video enhancement techniques. The captured videos 314 may be processed according to these techniques, for example, to visually amplify pulsatile motions captured by the original videos. The parameters for amplification, such as frequency bands of interest to amplify, can be automatically determined with the captured videos 314 by detecting a heart rate of the person 102 through temporal chroma changes or other visible motion. Extraneous motion, such as global motion due to patient movement, can be suppressed to reduce clutter. The visually amplified pulsatile motions in the reconstructed video 316 can be analyzed by the AJR-testing manager 312 as described below to measure the person 102's JVP. Accordingly, the AJR-testing manager 312 includes or has access to jugular venous pulse measurements 318 (JVP measurements 318). The AJR-testing manager 312 also includes or has access to AJR test results 320, which can be generated based on comparisons made by the AJR manager 312 of the JVP measurements 318 to one or more AJR-test thresholds.

The AJR-testing manager 312 represents functionality to employ the camera 302 to capture video in conjunction with a session for performing an AJR test of the person 102. As used herein, the term "session" refers to a period of time during which the AJR-testing device 106 synchronizes the application of pressure to the person 102's abdomen with the capture of video of their neck for the purpose of performing an AJR test. Generally, the length of a session corresponds to a predetermined amount of time associated with conducting AJR tests, e.g., typically pressure is applied to a person's abdomen for 10-15 seconds to conduct an AJR test. Accordingly, the camera 302 is employed to capture video of the person 102 at least while pressure is applied to the person 102's abdomen. The camera 302 can also be employed to capture video of the person 102 for predetermined amounts of time both before and after pressure is applied to the person 102's abdomen, so that a difference can be observed in the person 102's JVP and jugular distension at a time before the pressure is applied to the person 102's abdomen and at a time after the pressure is applied. In some cases where the AJR-testing manager 312 is unable to confidently detect a location of the JVP before pressure is first applied (e.g., the AJR testing manager is unable to detect the JVP location with sufficient confidence to pass a JVP detectability threshold), an additional short pressure cycle can be used to confirm the JVP location by monitoring the response to the applied pressure. Once the initial location is confirmed, the test sequence can continue. In some embodiments, the AJR-testing device 106 is capable of alerting a medical professional using the AJR-testing device 106 when a sufficient amount of video has been captured and the session can be ended. By way of example, the AJR-testing device 106 can be configured to alert the person 102 audibly, such as by beeping, visually, such as by causing an indication to be presented on the user interface 114, and/or by touch, such as by vibrating.

In one example, the AJR-testing manager 312 initiates an AJR test by communicating an indication to the abdominal pressure cuff 108 wrapped around the person 102 to apply pressure to their abdomen. The AJR-testing manager 312 may do so, for example, after it receives one or more readiness indications from the abdominal pressure cuff 108 indicating that it is ready to apply pressure to the person 102's abdomen. In this example, the AJR-testing manager 312 employs the camera 302 to capture video of a right side of the person 102's neck while the abdominal pressure cuff 108 applies pressure to the person 102's abdomen.

As mentioned above, the right side of the person 102's neck may be captured because it is where the external and internal jugular veins of the person 102 are located. Accordingly, the right side of the person 102's neck is where pulsatile motions indicative of JVP can be observed. Some pulsatile motions occurring on the right side of the person 102's neck may be too subtle to be perceptible by a medical professional who views the captured videos 314, for example, when the person 102 is obese and their external and internal jugular veins lie deep underneath their skin. These motions can be detected and amplified, however, through the application of video-processing techniques.

The AJR-testing manager 312 also represents functionality to process the captured videos 314 to generate the reconstructed videos 316, in which pulsatile motions of the person 102's venous system are amplified. To do so, the AJR-testing manager 312 is capable of applying one or more video motion amplification techniques to the captured videos 314. The result of such techniques is to amplify motions (e.g., pulsatile motions) from the captured videos 314 that are imperceptible to the human eye so that they are visible to the human eye in the reconstructed videos 316. Such techniques are also effective to improve a contrast and a signal-to-noise ratio of pulsatile motion due to the venous system for downstream processing and analysis by the AJR-testing manager 312. In addition to the motion amplification techniques, the AJR-testing manager 312 is capable of applying one or more other video enhancement techniques (e.g., temporal or spatial filtering, non-linear contrast enhancement, and so forth) to further enhance either the visibility or the detectability of the JVP signal.

When the captured videos 314 are processed according to such techniques, the AJR-testing manager 312 is capable of generating, and thus displaying, the reconstructed videos 316 in real time. By "real time" it is meant that the delay between a motion occurring, which a medical professional viewing the person 102 can observe, and presentation of the visually-amplified motion on the display 304 in a reconstructed video is imperceptible or nearly imperceptible to the medical professional. Consequently, the reconstructed videos 316 can be displayed on the display 304 as part of the user interface 114 while the camera 302 is being used to capture video. In this way, the user interface 114 presented via the display 304 can act as a viewfinder for the camera 302. It should be noted that a variety of video motion amplification or video enhancement techniques may be applied to generate the reconstructed videos 316 without departing from the spirit or scope of the techniques described herein. Additionally, the AJR-testing manager 312 is capable of automatically detecting and indicating a location of the JVP in real time video by displaying one or more graphical overlays identifying the location.

In addition to real-time display, the AJR-testing manager 312 is also capable of playing back the reconstructed videos 316 at other speeds or at different times. For example, the AJR-testing manager 312 can enable a reconstructed video to be played back in slow motion. The user interface 114 may enable a user of the AJR-testing device 106 to choose a speed at which to playback the reconstructed video, e.g., ½ speed, ¼ speed, ⅛ speed, and so on. The user interface 114 may also include controls that enable the user to pause the reconstructed video, skip forward or backward (at different speeds), return to a live feed, and so forth. By playing back the reconstructed video in slow motion and allowing it to be paused at different locations during playback, the user interface 114 can enable a medical professional to manually measure characteristics of pulsatile motions that are indicative of the person 102's JVP. To enable such measuring, the user interface 114 may include different graphical overlays as shown in FIG. 1, including overlays indicative of timing, a vertical orientation, and markers for measuring distances, e.g., a height blood rises in the person 102's jugular vein as a result of the applied pressure.

Regardless of whether motion amplification techniques are applied, the pulsatile motions captured in the captured videos 314 can be measured by the AJR-testing manager 312. The AJR-testing manager 312 can be configured to measure the pulsatile motions from the captured videos 314 and the reconstructed videos 316. For example, the AJR-testing manager 312 can determine a frame in which a given pulsatile motion has reached a peak height, and associate a timestamp with this frame. By determining when multiple pulsatile motions reach peak heights, the AJR-testing manager 312 can measure a JVP of the person 102. In other words, the AJR-testing manager 312 can determine a rate of the JVP, such as in beats-per-minute (BPM) or using some other unit. In some implementations, the JVP motion can be captured over entire cardiac cycles, allowing for tracing of the entire JVP waveform and the labeling of "classic" features, such as the 'a', 'c', and 'v' ascents as well as the 'x' and 'y' descents. By determining the person 102's JVP over the course of a captured video, the AJR-testing manager 312 can also determine changes that occur to the JVP throughout the video (dynamic responses of the JVP), such as whether the location of the JVP rises during the video, falls during the video, remains the same, and so on.

In addition to determining the person 102's JVP, the AJR-testing manager 312 can process the captured videos 314 (and the reconstructed videos 316) to measure other characteristics of the person 102's JVP and jugular distension that are pertinent to AJR tests. By way of example, the AJR-testing manager 312 can process the captured videos 314 (and the reconstructed videos 316) to determine peak heights of pulsatile motions indicative of JVP. Given this information, the AJR-testing manager 312 can compare the peak heights that occurred before pressure was applied to the person 102's abdomen to the peak heights that occur while pressure is applied. In this way, the AJR-testing manager 312 can determine a difference in the peak heights before pressure was applied (e.g., an average of the peak heights before pressure was applied) and the peak heights while the pressure is applied (e.g., an average of the peak heights while pressure is applied). Based on the difference, if any, the AJR-testing manager 312 can determine an amount the person 102's JVP rises or falls during an AJR test.

Further still, the AJR-testing manager 312 can process the captured videos 314 (and the reconstructed videos 316) to time the occurrence of particular conditions. By way of example, the captured videos 314 (and the reconstructed videos 316) can determine an amount of time that the person 102's peak heights of pulsatile motions indicative of JVP remain above a certain rise. To do so, the AJR-testing manager 312 can initiate and maintain one or more timers. The AJR-testing manager 312 can initiate a timer, for instance, when the person 102's JVP exceeds a threshold JVP rise, allow the timer to track an elapsed time, and then when the person 102's JVP falls below the threshold rise or the test ends, stop the timer. Based on the time the timer is stopped, the AJR-testing manager 312 can associate an elapsed time (e.g., as amount of time) with the occurrence of the person 102's JVP exceeding the threshold JVP.

It should be appreciated that, through an analysis of the captured videos 314 (and the reconstructed videos 316), the AJR-testing manager 312 can be configured to associate timestamps with a variety of different events and to associate elapsed times with the occurrence of different conditions without departing from the spirit or scope of the techniques described herein.

In processing the captured videos, the AJR-testing manager 312 can generate the JVP measurements 318. In general, the JVP measurements 318 represent any of a variety of measurements that can be used in conjunction with determining the results of an AJR test and that may be of interest to a medical professional reviewing the results of an AJR test. By way of example, the JVP measurements 318 can represent detected JVP, such as an average (e.g., including mean, median, mode) JVP throughout an AJR test, an average JVP before pressure was applied by the abdominal pressure cuff, an average JVP while pressure is applied by the abdominal pressure cuff 108, an average JVP after the abdominal pressure cuff 108 ceases applying pressure to the person 102's abdomen, and so on. In addition to average, JVPs the JVP measurements 318 can represent specific JVPs at different times throughout an AJR test (dynamic JVP responses), such that data indicative of a JVP determined at a particular time during an AJR test is generated. The JVP measurements 318 can also represent the above-discussed peak heights of pulsatile motions indicative of JVP and the elapsed times determined for the occurrence of AJR-pertinent conditions.

Using the JVP measurements 318, the AJR-testing manager 312 can determine a result of an AJR test and generate the AJR test results 320 based on the determination. To do so, the AJR-testing manager 312 can compare the JVP measurements 318 to multiple thresholds associated with AJR testing. By way of example, the AJR-testing manager 312 can compare the JVP measurements 318 to an initial JVP rise threshold, a sustained JVP rise threshold, and a JVP fall threshold to name a few. The initial JVP rise threshold, for instance, may be used to perform an initial comparison with a JVP detected during an AJR test. If the AJR-testing manager 312 compares the detected JVP to the initial JVP rise threshold and determines based on the comparison that the detected rise in JVP stays below the initial JVP rise threshold throughout the AJR test (e.g., before the pressure is applied, while the pressure is applied, and after application of the pressure is ceased), then the AJR-testing manager 312 can determine that the result of the AJR test is negative. For instance, if the observed JVP rises less than 3 centimeters and then falls down even while pressure on the abdomen is maintained the result of the AJR test is negative. The AJR-testing manager 312 can then generate data that indicates a negative result and associate other information with the result such a timestamp indicating when the AJR test was performed.

The AJR-testing manager 312 can also compare the rise in JVP detected throughout the AJR (and relative to a baseline measurement of the JVP) to the sustained JVP rise threshold. If, for example, the comparison indicates that the person 102's JVP does rise above the initial JVP rise threshold during the test, but then falls below the sustained JVP rise threshold within a set time interval (typically at least 10 seconds) while pressure is still applied, then the result of the test is again determined to be negative. If the person's JVP remains above the sustained JVP rise threshold for the set time interval, however, a positive test result may be determined.

The AJR-testing manager 312 can also compare a descent in JVP detected during the AJR test to a JVP descent threshold. If the comparison indicates that the rise in the JVP falls by at least the threshold amount within a short time interval after pressure is released, a positive result is generated. For instance, if the JVP observed by the AJR-testing manager 312 remains elevated above 3 centimeters during the 10 seconds of sustained pressure and drops abruptly by more than 4 centimeters upon release of the pressure, the AJR-testing manager determines that the result of the AJR test is positive. Accordingly, the AJR-testing manager 312 can generate data that indicates a positive result for the AJR test and associate other information with the test result. The ability of the AJR-testing manager 312 to efficiently and reproducibly quantify the response of the JVP to the applied pressure will allow for the development of new thresholds to improve sensitivity and specificity as well as more diagnostic resolution than mere binary—pass or fail—results. For example, a peak height, rise and fall times, and other metrics may be quantified and trended over time. These other metrics may include any other information a medical professional might expect or like to review in conjunction with a binary AJR test result.

In addition to comparing the detected JVP and jugular distension to a variety of thresholds, the AJR-testing manager 312 is also configured to analyze the captured videos 314 to check the test for errors that may skew test results. By way of example, the AJR-testing manager 312 can process the captured videos 314 to confirm that the person 102 is not performing a Valsalva maneuver. Further, the AJR-testing manager 312 is configured to perform a system self-test to detect conditions that may lead to erroneous test results, such as poor lighting, bad image quality, excessive motion, faults with the abdominal pressure cuff 108, and so forth. When a self-test reveals such conditions, the AJR-testing manager 312 can warn a user of the conditions by displaying a warning, e.g., indicating the condition and that the condition may lead to erroneous results in an AJR test.

The AJR-testing manager 312 also represents functionality to trend measurements taken during the automated AJR tests (e.g., measurements beyond mere binary test results) over time (e.g., over the course of a day, a week, weeks, or months) to detect changes in a functional status of the person 102's cardiac performance.

When an AJR test is completed and the results have been generated, the AJR-testing manager 312 can configure the user interface 114 to present the results. In so doing, the AJR-testing manager 312 can access a corresponding test result and measurements from the AJR test results 320 and the JVP measurements 318, respectively. The AJR-testing manager 312 can then configure the user interface 114 to include the corresponding test result (e.g., an indication of a positive, negative, or indeterminate AJR test) and the corresponding measurements. The AJR-testing manager 312 can also configure the user interface 114 to include historical information, so that a user can compare a most recently conducted AJR test to previously conducted AJR tests. To do so, the AJR-testing manager 312 can access historical test results and measurements from the AJR test results 320 and the JVP measurements 318, respectively. In addition to merely presenting historical data, the AJR-testing manager 312 can configure the user interface 114 to indicate trends between historical AJR tests and the most recently conducted AJR test, such as whether the test results have improved over time (e.g., whether there have been more or more frequent negative tests), the test results have declined over time, the AJR-pertinent measurements have improved or declined over time, and so on.

In addition to presenting captured video and test results, the user interface can also present information regarding how to perform an AJR test. For example, the AJR-testing manager 312 can configure the user interface 114 to present instructions to a user such as medical professional that indicate how to position the abdominal pressure cuff 108 on the person 102 so that an AJR test can be performed.

Figure 4A:
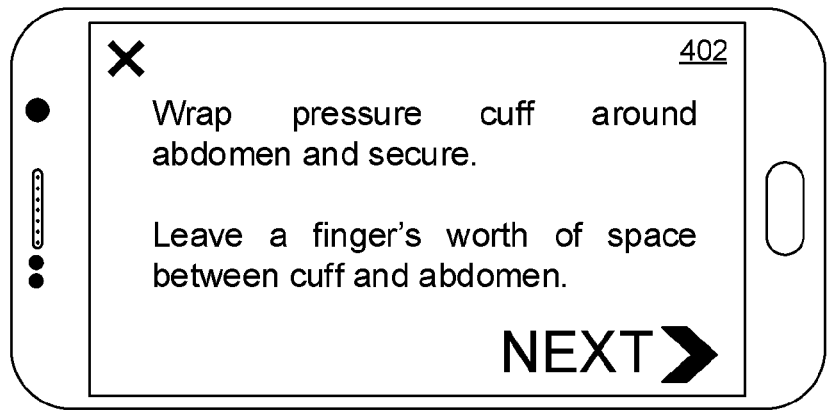
FIG. 4A illustrates an example user interface presented to instruct a user how to put a suitably configured pressure cuff on a patient in conjunction with automated AJR testing.
Figure 4B:
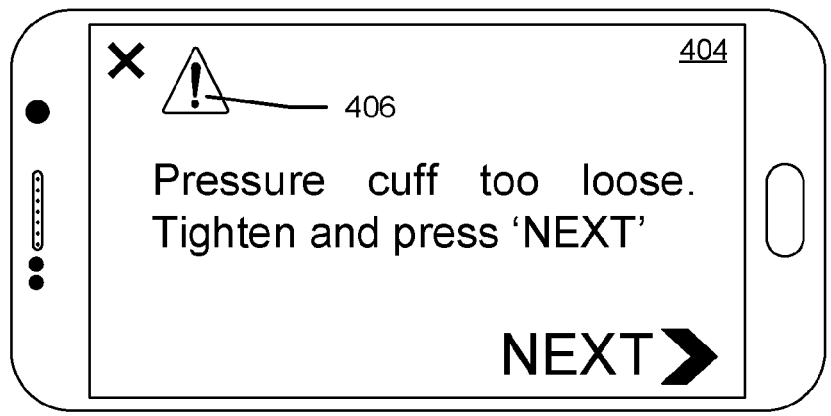
FIG. 4B illustrates another example user interface presented to warn the user that the pressure cuff is not positioned on the person to enable automated AJR testing.
Figure 4C:
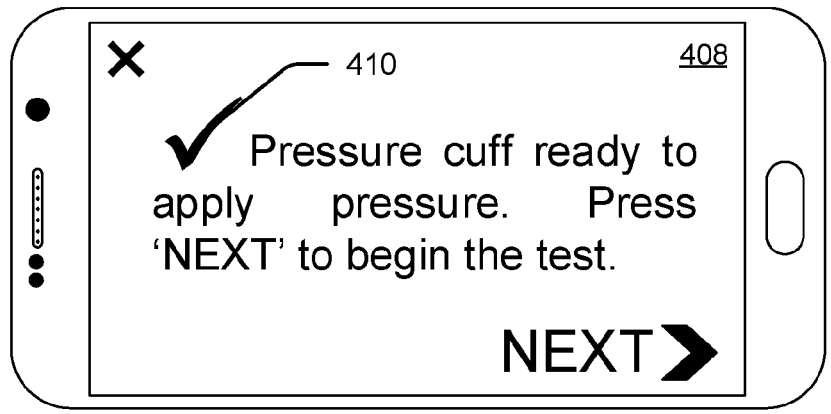
FIG. 4C illustrates another example user interface presented to inform the user the pressure cuff is properly positioned on the patient to enable automated AJR testing.

For context, consider FIGS. 4A-4C, which illustrate examples of user interfaces that can be presented in conjunction with an AJR test to instruct a user how to properly position the abdominal pressure cuff 108 on a subject of the test.

The example user interface 402 includes instructions that indicate how to put a suitably configured pressure cuff on a patient in conjunction with automated AJR testing. In addition to the instructions, the user interface 402 is illustrated with a next button, which can be selected by a user to indicate that the abdominal pressure cuff 108 has been put on the person 102 as instructed in the user interface 402. Based a user selection of the next button, the pressure manager 204 and the AJR-testing manager 312 may be operable to determine whether the abdominal pressure cuff 108 has been properly positioned on the person 102.

By way of example, the AJR-testing manager 312 can send a request to the pressure manager 204 to check the positioning of the abdominal pressure cuff 108. Based on the request, the pressure manager 204 can employ the pressure cuff positioning sensors 208 to collect information about the positioning of the abdominal pressure cuff 108 around the person 102. The pressure manager 204 may then cause communication of one or more readiness indications to the AJR-testing device 106 that include information about the positioning of the abdominal pressure cuff 108. The information included in the readiness indications can indicate a readiness of the abdominal pressure cuff 108 to apply pressure to the person 102's abdomen for an AJR test, e.g., the indicators can indicate that the abdominal pressure cuff 108 is ready to apply the pressure or is not ready.

In one or more scenarios, the AJR-testing manager 312 processes the readiness indications to determine that the abdominal pressure cuff 108 is not ready for an AJR test to be performed. The readiness indications may indicate that the abdominal pressure cuff 108 is not aligned so that pressure can be applied to a particular region of the person 102's abdomen, is not tight enough to enable a particular amount of pressure (e.g., 20-35 mmHg) to be applied to the particular region (or is too tight), and so on. When readiness indications indicate that the abdominal pressure cuff 108 is not ready to apply the pressure, the AJR-testing manager 312 can determine instructions to convey to a user to adjust the abdominal pressure cuff 108 so that it is positioned to apply the pressure to the particular region of the person 102's abdomen. The readiness indications as generated by the pressure manager 204 may indicate how to reposition the abdominal pressure cuff 108. In such scenarios, the AJR-testing manager 312 may simply extract the indications regarding repositioning for inclusion in a user interface. In other scenarios, however, the readiness indications received by the AJR-testing manager 312 may not specifically indicate how to reposition the abdominal pressure cuff 108, but may indicate the positioning of the abdominal pressure cuff 108 relative to a target positioning. In these scenarios, the AJR-testing manager 312 may determine from the indications of relative position to a target positioning how the abdominal pressure cuff 108 needs to be adjusted so that it is positioned in the target position. The AJR-testing manager may, in such scenarios, generate the adjustment instructions for inclusion as part of a user interface.

The example user interface 404 includes a notification indicating that the abdominal pressure cuff is not wrapped around the user in a manner that enables an AJR test to be performed properly. The user interface 404 also includes instructions for adjusting the abdominal pressure cuff 108 so that it can enable an AJR test to be performed without error. Warning icon 406 can be included as part of the user interface 404, as a further visual indicator to alert a test administrator that the abdominal pressure cuff 108 is not properly positioned. Like the user interface 402, the user interface 404 is illustrated with the next button, which is selectable to indicate that the abdominal pressure cuff 108 has been adjusted as instructed by the user interface 404. Based on a selection of the next button from the user interface 404, the pressure manager 204 and the AJR-testing manager 312 may again be operable to determine whether the abdominal pressure cuff 108 has been properly positioned on the person 102. As long as the abdominal pressure cuff 108 is not properly wrapped around the person 102, user interfaces warning the user of the incorrect positioning and instructing the user how to correctly wrap the abdominal pressure cuff 108 around the person may continue to be presented.

When the abdominal pressure cuff 108 is properly wrapped around the person 102, however, the readiness indications may indicate that the abdominal pressure cuff 108 is ready to apply the pressure for an AJR test. The example user interface 408 includes a notification that may be presented in this scenario. In particular, the user interface 408 illustrates a notification that indicates the abdominal pressure cuff 108 is ready to apply pressure to the person 102's abdomen for an AJR test. As illustrated, the user interface 408 also includes a confirmatory icon 410 that serves as a simple visual indicator to indicate the abdominal pressure cuff 108 is ready for performing an AJR test. Like user interfaces 402, 404, user interface 408 is illustrated with a next button. The next button of user interface 408 represents functionality to receive input from a user to initiate an AJR test, such that when a user selects the next button from user interface 408 the AJR test is begun. As a result of such selection, the AJR-testing manager 312 employs the camera 302 to capture video of the person 102's neck, and then at an appropriate time communicates an indication to the abdominal pressure cuff 108 to initiate application of pressure to the person 102's abdomen.

The AJR-testing manager 312 can generate a variety of other user interfaces within the spirit and scope of the techniques described herein. By way of example, the AJR-testing manager 312 may configure user interfaces that instruct a user how to position the AJR-testing device 106 so that the camera 302 can capture video of a target region of the person 102's neck. By way of example, the AJR-testing manager 312 can display a scene captured by the camera 302 and also present overlays on the user interface instructing the user to pan right, pan left, zoom in, zoom out, and so on, to capture the target portion of the person 102's neck. Further, the AJR-testing manager 312 can configure user interfaces that warn a user of dangerous conditions. When the user is a medical professional administering the AJR test, user interfaces can be generated based on analysis of the captured videos 314 that indicate the dangerous conditions and measurements that describe the condition. In this way the medical professional may be able to determine a course of treatment for the person 102. If the test is being self-administered, however, the AJR-testing manager 312 can configure a user interface that indicates to contact a medical professional immediately, and gives the user instructions such as to rest, take a certain medication, and so on. In scenarios in which the test is self-administered, the AJR-testing manager 312 may automatically contact a medical professional on behalf of the person 102. In such scenarios, the AJR-testing manager 312 may still configure the user interface with instructions that will help alleviate a determined dangerous condition or advise a user in an attempt to reduce a likelihood that the dangerous condition results in a more serious event, e.g., congestive heart failure decompensation. These instructions may include an adjustment in medical prescription (e.g., to increase or decrease the use of diuretics) or a recommendation to schedule a visit to a clinic for a follow-up. Such instructions may also be based on trends determined by the AJR-testing manager 312 from the measurements taken during multiple AJR tests over time.

By enabling AJR to be tested automatically, the AJR-testing device 106 can be used to enable telemedicine. In other words, the person 102 may be able to stay at home and receive health care formerly available solely in a hospital or specialized clinic. Not only may data indicative of the AJR test results 320 be communicated to a medical professional associated with the person 102, but the captured and reconstructed videos, 314 and 316 respectively, can also be communicated to the medical professional to enable them to remotely analyze the person 102's JVP. Further, the techniques described herein enable home or nursing care to be provided by medical professionals other than physicians.

These and other capabilities, as well as ways in which entities of FIGS. 1-4C act and interact, are set forth in greater detail below. These entities may be further divided, combined, and so on. The environment 100 of FIG. 1 and the detailed illustrations of FIGS. 2-4C illustrate some of many possible environments capable of employing the described techniques.

Example Methods

Figure 5:
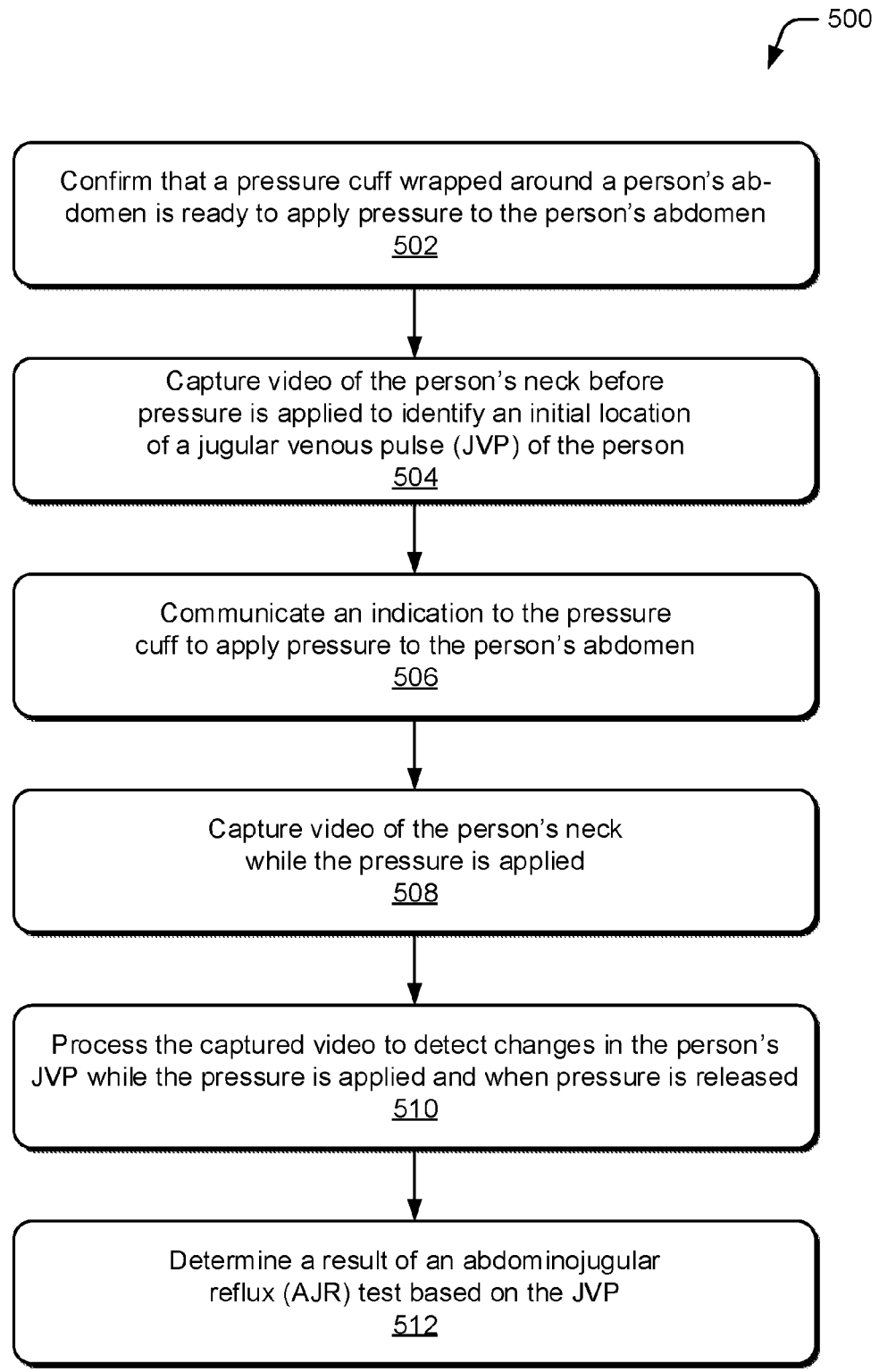
FIG. 5 illustrates a method to perform an automated AJR test using a suitably configured abdominal pressure cuff and a video recording of a person's neck.
Figure 6:
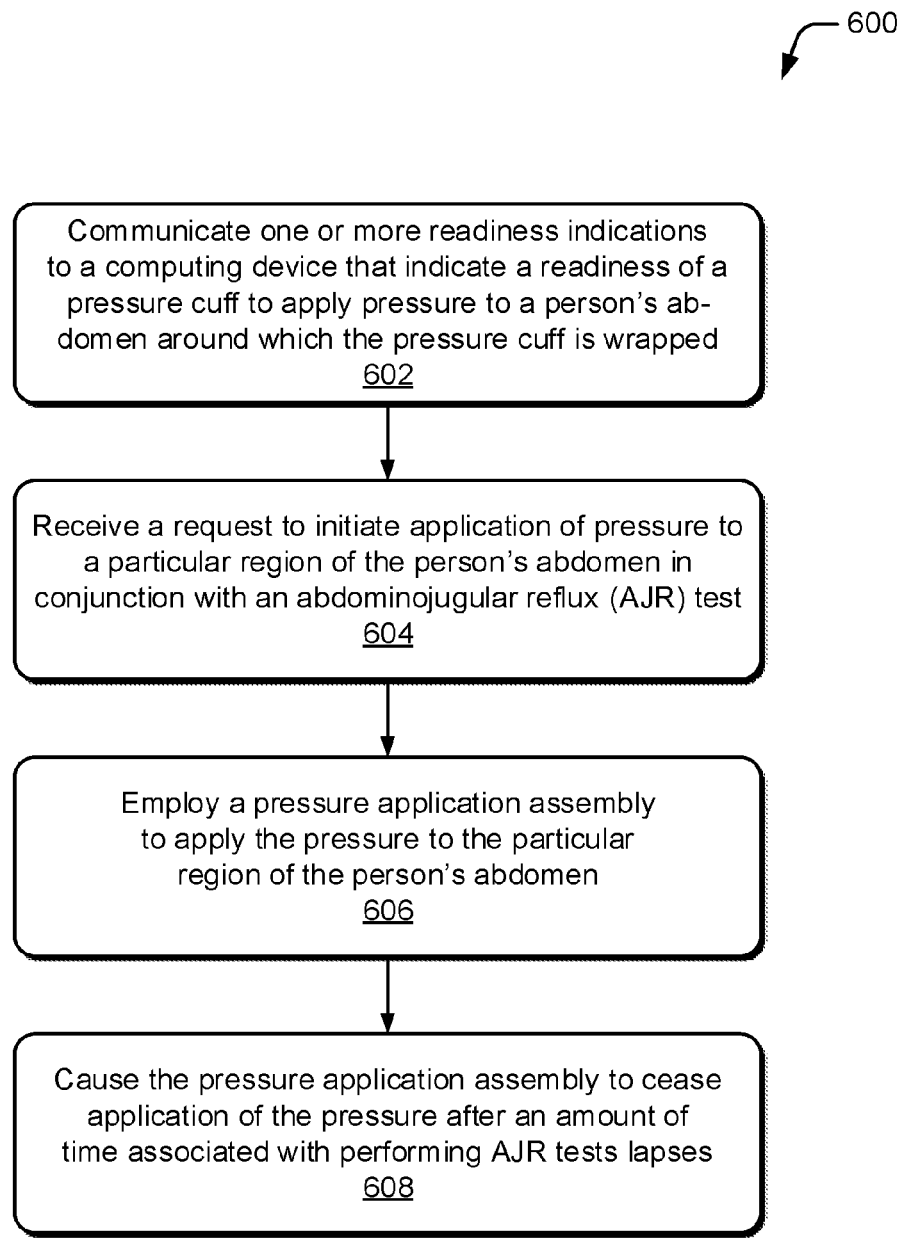
FIG. 6 illustrates a method to apply pressure by an abdominal pressure cuff to a particular region of a person's abdomen in conjunction with an AJR test.

FIGS. 5 and 6 depict methods enabling or using automated abdominojugular reflux testing. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2 and 3, reference to which is made for example only. The techniques are not limited to performance by one entity or multiple entities operating on one device.

FIG. 5 depicts method 500, which describes manners in which to perform an automated AJR test using a suitably configured abdominal pressure cuff and a video recording of a person's neck.

At 502, it is confirmed that a pressure cuff wrapped around a person's abdomen is ready to apply pressure to the person's abdomen. By way of example, the AJR-testing device 106 receives one or more readiness indications from the abdominal pressure cuff 108 indicating that it is ready to apply pressure to the person 102's abdomen.

At 504, video of the person's neck is captured before pressure is applied to identify an initial location of a jugular venous pulse (JVP) of the person. In accordance with the principles discussed herein, a heart rate, a respiration rate, and other metrics may also be identified from the video. By way of example, the AJR-testing manager 312 employs the camera 302 of the AJR-testing device 106 to capture video of the right side of the person 102's neck before pressure is applied to the person 102's abdomen. From this video, the AJR-testing manager 312 identifies an initial location of the person 102's JVP. The AJR-testing manager 312 can also identify other metrics from the video, such as the person 102's heart rate, respiration rate, and so on. If the AJR-testing manager 312 determines that the person 102's JVP is not visible in this initially captured video, the AJR-testing manager 312 may communicate abdominal cuff control data 112 to the abdominal pressure cuff 108 that indicates to perform a short pressure cycle to cause jugular distension in the person 102's neck so that the initial location of the JVP can be confirmed. Once it is confirmed that the abdominal pressure cuff is correctly situated around the person 102's abdomen and the person 102's initial JVP is located, the AJR test may proceed.

At 506, an indication is communicated to the pressure cuff to apply pressure to the person's abdomen. By way of example, the AJR-testing manager 312 generates an indication to initiate application of pressure to the person 102's abdomen. The AJR-testing manager 312 causes this indication to be communicated as part of the abdominal cuff control data 112 to the abdominal pressure cuff 108 so that it can apply pressure to the person 102's abdomen. The AJR-testing manager 312 generates and sends this indication after confirming the abdominal pressure cuff 108 is ready to apply the pressure, after the person 102's initial JVP is located, and also responsive to receiving input via the user interface 114 to initiate the AJR test.

With regard to receiving the input via the user interface 114, for example, the input may correspond to a touch selection made by a user (e.g., a medical professional) of a button to initiate an AJR test. This button may be generated and presented by a vitals-monitoring application of the AJR-testing device 106. The AJR-testing manager 312 may also employ the camera 302 to initiate an AJR test, and thus capture video of the person 102 in response to other initiation actions. For example, the AJR-testing device 106 may be set up in a fixed position relative to the person 102, such as on a tripod, and automatically initiate an AJR test of the person 102 at predetermined intervals. When the AJR-testing device 106 is set up in this way, AJR tests may be performed for the person 102 without any user interaction other than to position the AJR-testing device 106 initially At 508, video of the person's neck is captured while the pressure is applied. By way of example, while the abdominal pressure cuff 108 applies 20-35 mmHg of pressure to the person 102's abdomen, the AJR-testing manager 312 employs the camera 302 of the AJR-testing device 106 to capture video of the right side of the person 102's neck. The AJR-testing manager 312 also employs the camera 302 to capture the video before application (in addition to employing the camera to locate the person 102's JVP) and after application of the pressure so that changes in the JVP can be observed and analyzed.

At 510, the captured video is processed to detect changes in the JVP of the person while application of pressure is initiated and sustained and when the pressure is released. By way of example, the AJR-testing manager 312 processes the captured videos 314 to generate the reconstructed videos 316. As discussed above, in the reconstructed videos 316 pulsatile motions that occur in the person 102's neck may be visually amplified, such as by processing the captured videos 314 using one or more video motion amplification or other enhancement techniques. The AJR-testing manager 312 processes at least one of the captured videos 314 or the reconstructed videos 316 to detect changes in a JVP of the person 102. For instance, the AJR testing manager 312 measures a change in location of the JVP over time as the pressure is applied, sustained, and released. In scenarios in which the reconstructed videos 316 are available, the AJR-testing manager 312 detects the person 102's JVP using the reconstructed videos 316. In scenarios in which the reconstructed videos are not available, however, the AJR-testing manager 312 simply analyzes the captured videos 314 to detect changes in the person 102's JVP.

At 512, a result of the AJR test is determined based on the JVP. By way of example, the AJR-testing manager 312 determines whether the AJR test result is positive or negative. To do so, the AJR-testing manager 312 compares the change in JVP detected at 510 to one or more thresholds. By way of example, the AJR-testing manager 312 accesses data from the JVP measurements 318 corresponding to the JVP detected at 510 and compares this to the one or more thresholds for AJR tests. One threshold may indicate an initial rise threshold. The AJR-testing manager 312 compares the detected change in JVP to this threshold. If the detected rise in JVP remains below the initial rise threshold while pressure is applied to the person 102's abdomen, the AJR-testing manager 312 determines a negative test result as discussed above. As also discussed above, the AJR-testing manager 312 compares detected changes in JVP to other thresholds, such as a minimum sustained rise threshold and a minimum descent threshold. The AJR-testing manager makes these comparisons, in part, to determine a positive or negative result of the test.

Broadly speaking, when the AJR-testing manager 312's comparison of the detected change in JVP to the thresholds indicates that the JVP rises less than 3 centimeters and then falls even while pressure is maintained, the AJR-testing manager 312 determines a negative result for an AJR test. When the AJR-testing manager 312's comparison of the detected JVP to the thresholds indicates that the observed JVP remains elevated above 3 centimeters during 10 seconds of sustained pressure and drops abruptly by more than 4 centimeters upon release of the pressure, then the AJR-testing manager 312 determines a positive result for the AJR test.

The result may then be stored for later use, presented in a user interface, and so on. By way of example, the AJR-testing manager 312 may generate the user interface 114 to include the result of the AJR test determined at 512. Along with the result, the user interface 114 may present additional information pertinent to the AJR test as described above. The AJR-testing manager 312 generates data indicative of the result, which can be stored as the AJR test results 320. It is to be appreciated that the JVP measurements 318 and the AJR test results 320 may, in one or more implementations, be stored in storage that is not part of the AJR-testing device 106, such as in a remote database that is accessible through one or more communication networks.

FIG. 6 depicts method 600, which describes manners in which to apply pressure by an abdominal pressure cuff to a particular region of a person's abdomen in conjunction with an AJR test.

At 602, one or more readiness indications is communicated to a computing device. In accordance with the principles discussed herein the readiness indications indicate a readiness of a pressure cuff to apply pressure to a person's abdomen around which the pressure cuff is wrapped for an AJR test. By way of example, the transceiver 202 of the abdominal pressure cuff 108 communicates the readiness indications to the AJR-testing device 106 as packets of the abdominal cuff control data 112. As described in the discussion of FIGS. 4A-4C, the readiness indications can indicate a readiness of the abdominal pressure cuff 108 to apply pressure to the person 102's abdomen for AJR testing. In particular, the readiness indications can indicate that the abdominal pressure cuff 108 is ready to apply the pressure to the person 102's abdomen, or that the abdominal pressure cuff 108 is not ready to do so, e.g., it is not positioned to enable an AJR test to be properly performed. In the scenario in which the abdominal pressure cuff 108 is not ready to apply the pressure, the readiness indications may indicate information regarding a position of the abdominal pressure cuff relative to a target position or may indicate how to adjust the abdominal pressure cuff 108 so that it can be positioned to enable an AJR test to be performed.

At 604, a request to initiate application of pressure to a particular region of the person's abdomen in conjunction with an AJR test is received. By way of example, the abdominal pressure cuff 108 receives a request in the abdominal cuff control data 112 communicated from the AJR-testing device 106 to initiate application of pressure for an AJR test.

At 606, a pressure application assembly of pressure cuff is employed to apply the pressure to the particular region of the person's abdomen. By way of example, the pressure manager 204 employs the pressure application assembly 206 to apply pressure to the particular region of the person 102's abdomen. When the pressure application assembly 206 is inflatable, for instance, the pressure manager 204 causes the pressure application assembly 206 to inflate so that it applies a slow, steady pressure in a range of 20-35 mmHg to the particular region of the person 102's abdomen.

At 608, the pressure application assembly ceases application of the pressure after an amount of time associated with performing AJR tests lapses. By way of example, the pressure manager 204 causes the pressure application assembly 206 to cease applying pressure to the particular region of the person 102's abdomen. Returning to the case in which the pressure application assembly 206 is inflatable, the pressure manager 204 causes the pressure application assembly 206 to deflate so that the 20-35 mmHg of pressure is no longer applied to the particular region of the person 102's abdomen. The pressure manager 204 may itself keep track of the time the pressure application assembly 206 applies pressure to the person 102's abdomen, and cause the abdominal pressure cuff 108 to cease applying pressure when the tracked time indicates that a time period associated with AJR testing had lapsed. Alternately, the pressure manager may receive an indication from the AJR-testing device 106 that indicates to stop applying the pressure. Accordingly, the pressure manager 204 may cause the pressure application assembly 206 to cease applying the pressure responsive to the received indication. In either case, the pressure manager 204 may cause the pressure application assembly 206 to cease applying the pressure to the person 102's abdomen after a period of time associated with AJR testing (10-15 seconds) lapses.

Through communication between the AJR-testing device 106 and the abdominal pressure cuff 108, the application of pressure and the capturing of video for an AJR test is synchronized so that video can be captured while the pressure is applied to the person 102's abdomen. In one or more implementations, however, the abdominal pressure cuff 108 may be deployed to apply the pressure (e.g., by pressing a button on the pressure cuff) without synchronization to an AJR-testing device. Rather, a medical professional may observe the pulsatile motions in the person 102's neck while the abdominal pressure cuff 108 applies pressure to manually determine a result of an AJR test.

The preceding discussion describes methods relating to automated abdominojugular reflux testing. Aspects of these methods may be implemented in hardware (e.g., fixed logic circuitry), firmware, software, manual processing, or any combination thereof. These techniques may be embodied on one or more of the entities shown in FIGS. 1-3 and 7 (computing system 700 is described in FIG. 7 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 7:
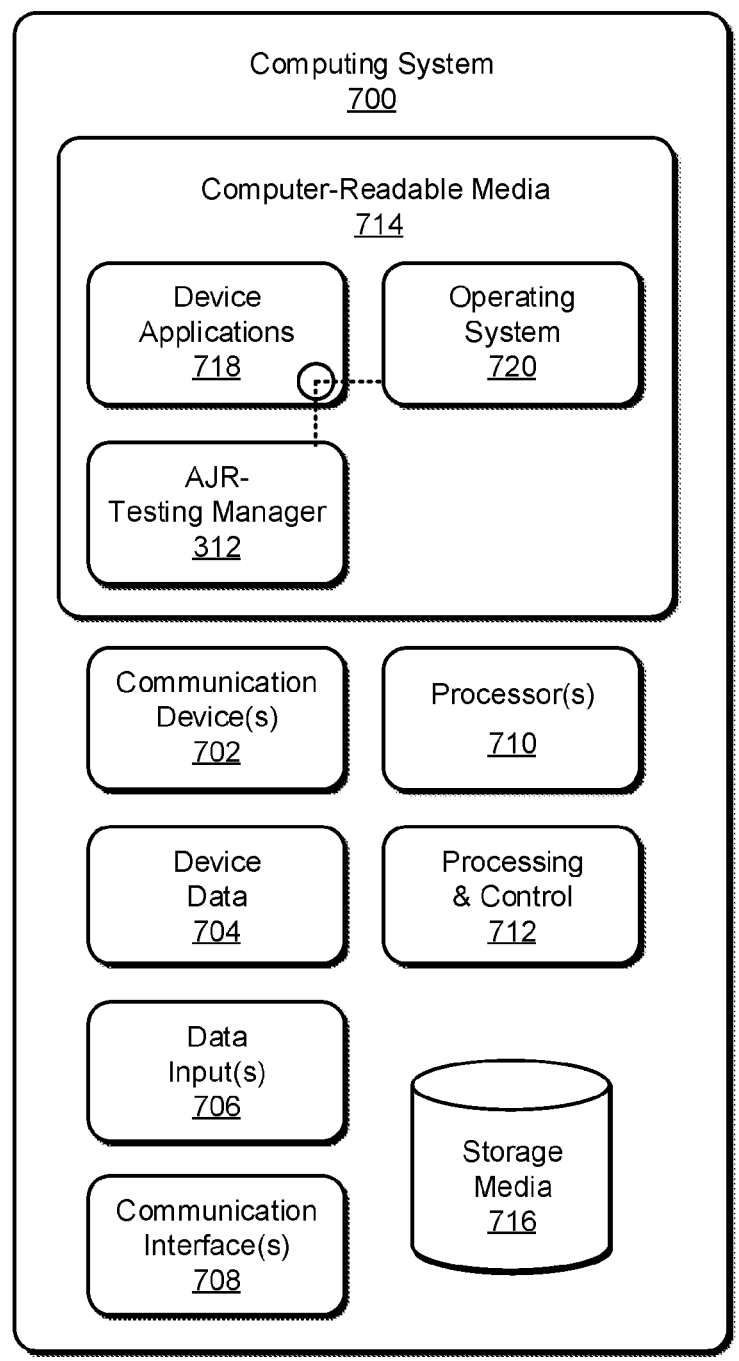
FIG. 7 illustrates an example computing system embodying, or in which techniques may be implemented that enable use of, automated abdominojugular reflux testing.

FIG. 7 illustrates various components of example computing system 700 that can be implemented as any type of client, server, and/or computing device as described with reference to the previous FIGS. 1-6 to implement automated abdominojugular reflux testing. In embodiments, computing system 700 can be implemented as one or a combination of a wired and/or wireless wearable device, System-on-Chip (SoC), and/or as another type of device or portion thereof. Computing system 700 may also be associated with a user (e.g., a person) and/or an entity that operates the device such that a device describes logical devices that include users, software, firmware, and/or a combination of devices.

Computing system 700 includes communication devices 702 that enable wired and/or wireless communication of device data 704 (e.g., received data, data that is being received, data scheduled for broadcast, data packets of the data, etc.). Device data 704 or other device content can include configuration settings of the device, media content stored on the device, and/or information associated with a user of the device. Media content stored on computing system 700 can include any type of audio, video, and/or image data, including complex or detailed results of automated AJR-testing acts. Computing system 700 includes one or more data inputs 706 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 700 also includes communication interfaces 708, which can be implemented as any one or more of a serial and/or parallel interface, a wireless interface, any type of network interface, a modem, and as any other type of communication interface. Communication interfaces 708 provide a connection and/or communication links between computing system 700 and a communication network by which other electronic, computing, and communication devices communicate data with computing system 700.

Computing system 700 includes one or more processors 710 (e.g., any of microprocessors, controllers, and the like), which process various computer-executable instructions to control the operation of computing system 700 and to enable techniques for, or in which can be embodied, automated abdominojugular reflux testing. Alternately or in addition, computing system 700 can be implemented with any one or combination of hardware, firmware, or fixed logic circuitry that is implemented in connection with processing and control circuits which are generally identified at 712. Although not shown, computing system 700 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 700 also includes computer-readable media 714, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 700 can also include a mass storage media device 716.

Computer-readable media 714 provides data storage mechanisms to store device data 704, as well as various device applications 718 and any other types of information and/or data related to operational aspects of computing system 700. For example, an operating system 720 can be maintained as a computer application with computer-readable media 714 and executed on processors 710. Device applications 718 may include a device manager, such as any form of a control application, software application, signal-processing and control module, code that is native to a particular device, a hardware abstraction layer for a particular device, and so on.

Device applications 718 also include any system components, engines, or managers to implement the techniques. In this example, device applications 718 include an AJR-testing manager 312.

Conclusion

Although embodiments of techniques using, and apparatuses enabling, automated abdominojugular reflux testing have been described in language specific to features and/or methods, it is to be understood that the subject of the appended claims is not necessarily limited to the specific features or methods described. Rather, the specific features and methods are disclosed as example implementations of these techniques.

What is claimed is:

1. A computer-implemented method for automating an abdominojugular reflux (AJR) test, the method comprising:
   communicating an indication to a pressure cuff wrapped around a person's abdomen to apply pressure to the person's abdomen;
   capturing video of the person's neck before, during, and after the pressure is applied to the person's abdomen;

processing the captured video to measure a dynamic response of a jugular venous pulse (JVP) of the person while application of the pressure is initiated, maintained, and released;

comparing measurements indicative of the dynamic response to one or more thresholds associated with AJR tests to determine a result of the AJR test that is indicative of cardiac functional performance of the person.

2. The computer-implemented method as described in claim 1, wherein the one or more thresholds include an initial JVP rise threshold, the measurements include a measurement indicative of an initial rise of the person's JVP, and the comparing includes comparing the measurement indicative of the initial rise to the initial JVP rise threshold.

3. The computer-implemented method as described in claim 2, wherein a negative AJR test result is determined if the initial rise of the person's JVP does not exceed the initial JVP threshold within a set time interval after the application of pressure is initiated.

4. The computer-implemented method as described in claim 2, wherein the initial rise threshold is 3 centimeters from an initial location of the person's JVP detected before the application of pressure.

5. The computer-implemented method as described in claim 1, wherein the one or more thresholds include a sustained JVP rise threshold, the measurements include metrics indicative of sustained rises of the person's JVP, and the comparing includes comparing metrics indicative of the sustained rises to the sustained rise threshold.

6. The computer-implemented method as described in claim 5, wherein a negative AJR test result is determined if the metrics indicate that a sustained rise of the person's JVP falls below the sustained JVP rise threshold within a set time interval while the pressure is applied.

7. The computer-implemented method as described in claim 5, wherein a positive AJR test result is determined based, at least in part, on the metrics indicating that a sustained rise of the person's JVP remains above the sustained JVP rise threshold for a set time interval while the pressure is applied.

8. The computer-implemented method as described in claim 1, wherein the one or more thresholds include a JVP descent threshold, the measurements include a measurement indicative of a fall in the person's JVP after the application of pressure is released, and the comparing includes comparing the measurement indicative of the fall to the JVP descent threshold.

9. The computer-implemented method as described in claim 8, wherein a positive AJR test result is determined based, at least in part, on a comparison that indicates the person's JVP falls by at least the JVP threshold within a set time interval after the application of pressure is released.

10. The computer-implemented method as described in claim 1, wherein the application of pressure is maintained for a predetermined period of time in a range of 10-15 seconds.

11. The computer-implemented method as described in claim 1, further comprising:

receiving one or more readiness indications from the pressure cuff that indicate a readiness to apply the pressure to the person's abdomen; and responsive to the one or more readiness indications indicating that the pressure cuff is ready to apply the pressure, communicating to the pressure cuff the indication to apply the pressure to the person's abdomen.

12. The computer-implemented method as described in claim 11, further comprising communicating a request to the pressure cuff that requests the one or more readiness indications responsive to receiving a user input to initiate the AJR test.

13. A device comprising:

a transceiver to communicate with a pressure cuff wrapped around a person's abdomen to control pressure applied to the person's abdomen;

a video camera to capture video of the person's neck while the pressure is applied to the person's abdomen; and a processing system to implement an abdominojugular reflux (AJR) testing manager configured to:

process the captured video to measure characteristics of pulsatile motions that occur in the person's neck and are indicative of a jugular venous pulse (JVP) of the person;

compare measurements of the characteristics to one or more thresholds associated with AJR tests; and determine a result of an AJR test for the person based on the comparison.

14. The device as described in claim 13, wherein the one or more thresholds include at least one of an initial JVP rise threshold, a sustained JVP rise threshold, and a JVP descent threshold.

15. The device as described in claim 13, further comprising a display device to display at least one of:

instructions regarding how to position the pressure cuff around the person's abdomen;

feedback regarding a positioning of the pressure cuff around the person's abdomen;

instructions regarding how to position the device to enable the video camera to capture the video of the person's neck;

a reconstructed video of the person's neck in which visually amplified pulsatile motions are perceptible to the human eye, the reconstructed video generated by processing the captured video to visually amplify the pulsatile motions that occur in the person's neck using one or more video motion amplification or other video enhancement techniques;

the result of the AJR test for the person; and one or more messages based on the result of the AJR test.

16. A pressure cuff for abdominojugular reflux (AJR) testing, the pressure cuff comprising:

a band configured to wrap around a person's abdomen;

a pressure application assembly integral with the band to apply pressure to a particular region of the person's abdomen; and a processing system to implement a pressure application manager configured to:

employ the pressure application assembly to apply the pressure to the particular region of the person's abdomen in conjunction with an AJR test of the person; and cause the pressure application assembly to cease application of the pressure after an amount of time associated with performing AJR tests lapses.

17. The pressure cuff as described in claim 16, further comprising a transceiver to wirelessly communicate with a computing device configured to detect jugular distensions in the person's neck indicative of a jugular venous pulse (JVP) while the pressure application assembly applies the pressure to the particular region, a result of the AJR test being determinable based on the JVP.

18. The pressure cuff as described in claim 16, further comprising a transceiver to communicate over a wired communication connection with a computing device configured to detect jugular distensions in the person's neck indicative of a jugular venous pulse (JVP) while the pressure application assembly applies the pressure to the particular region, a result of the AJR test being determinable based on the JVP.

19. The pressure cuff as described in claim 16, further comprising a transceiver to communicate with another computing device to control the pressure cuff to initiate the application of pressure, release the pressure, and control a level of the pressure applied by the pressure cuff.

20. The pressure cuff as described in claim 16, further comprising one or more sensors to detect conditions indicative of a positioning of the pressure cuff relative to the person's abdomen, the detected conditions being usable to determine whether the positioning enables performance of the AJR test.

* * * * *